United States Patent [19]

Datta et al.

[11] Patent Number: 4,649,112

[45] Date of Patent: Mar. 10, 1987

[54] UTILIZATION OF XYLAN AND CORN FIBER FOR DIRECT FERMENTATION BY CLOSTRIDIUM ACETOBUTYLICUM

[75] Inventors: Rathin Datta, Chicago; Steven A. Lemmel, Bolingbrook, both of Ill.

[73] Assignee: CPC International Inc., Englewood Cliffs, N.J.

[21] Appl. No.: 659,931

[22] Filed: Oct. 11, 1984

[51] Int. Cl.$^4$ .......................... C12P 7/40; C12P 7/28; C12P 7/16; C12R 1/145
[52] U.S. Cl. .................................. 435/136; 435/150; 435/160; 435/842
[58] Field of Search ............... 435/136, 151, 160, 132, 435/134, 842, 150, 152, 154

[56] References Cited

U.S. PATENT DOCUMENTS

| | | |
|---|---|---|
| 1,315,585 | 9/1919 | Weizmann . |
| 1,744,958 | 1/1930 | Freiberg .............................. 435/151 |
| 2,377,197 | 5/1945 | Weizmann . |
| 2,417,801 | 3/1947 | Weizmann . |
| 4,326,032 | 4/1982 | Grove . |
| 4,378,434 | 3/1983 | Prentice et al. . |
| 4,521,516 | 6/1985 | Lemme et al. ...................... 435/152 |

FOREIGN PATENT DOCUMENTS 572643  10/1945  United Kingdom .

Primary Examiner—Charles F. Warren
Assistant Examiner—John E. Tarcza

[57] ABSTRACT

Butanol, acetone and fatty acids are produced by direct fermentation of a low-cost source of carbohydrates by Clostridium acetobutylicum. The carbohydrate source is selected from the group consisting of corn fiber, xylan, and mixtures of corn fiber and xylan.

8 Claims, No Drawings

UTILIZATION OF XYLAN AND CORN FIBER FOR DIRECT FERMENTATION BY CLOSTRIDIUM ACETOBUTYLICUM

FIELD OF THE INVENTION

This invention relates to a method for the production of butanol, acetone, and fatty acids by a direct fermentation process. The carbon source used for the fermentation is either the hemicellulose, xylan, or corn fiber, without any pretreatment or hydrolysis.

BACKGROUND OF THE INVENTION

The fermentation of carbohydrates by *Clostridium acetobutylicum* (hereafter abbreviated *C. acetobutylicum*) to form butanol and acetone was disclosed by Weizmann in U.S. Pat. No. 1,315,585. For many years, this process was used commercially for the preparation of butanol and acetone, and a certain amount of ethanol was obtained as a by-product.

Eventually, the microbial process was displaced by chemical processes which provide the same products using cheap fossil fuel raw materials. However, the gradual depletion of petroleum fossil fuel with the resultant increase in prices of petrochemical feedstocks has revived interest in the fermentation reaction that uses carbohydrates, which are renewable raw materials.

One reason why the economics of producing acetone and butanol by fermentation has been unattractive has been the cost of the ground corn or high quality molasses feedstock used as the carbohydrate source. This has led to a search for less-expensive feedstocks for the process.

A fermentation utilizing straw as a starting material is described in U.S. Pat. No. 2,417,801. According to this disclosure, a substantial portion of the hemicelluloses in the straw had to be hydrolyzed with an acid before they could be fermented. Hydrolysis of other cellulosic materials was said to release substances deleterious to the fermentation. It was further reported in this patent and in U.S. Pat. No. 2,377,197 that rice bran or wheat bran could be used as the carbohydrate feedstock for the fermentation with *C. acetobutylicum*. However, the principal carbohydrate that was fermented in these cases was the starch component of the brans, and only a small part of the hemicellulose present was used.

The corn wet-milling industry produces a fibrous residue after the bulk of the germ, starch and gluten is removed from the corn. This residue, known as corn fiber, amounts to about 10% of the dry weight of the corn. It contains about 30% starch, 35% hemicellulose, 15% cellulose and 12% protein with smaller amounts of other components. This fiber would be a low-cost fermentation feedstock if the microorganism causing fermentation could use the carbohydrates present in the fiber.

It has now been found that an asporogenic strain of *C. acetobutylicum*, Strain ATCC 39,236, is capable of fermenting the starch and a substantial portion of the hemicelluloses present in corn fiber. Furthermore, this strain of *C. acetobutylicum* can ferment the hemicellulose, xylan, without the need to hydrolyze this polysaccharide before conducting the fermentation.

SUMMARY OF THE INVENTION

In accordance with the present invention, there is provided a process for producing products selected from the group consisting of acetone, butanol and fatty acids by fermenting an aqueous medium containing a carbohydrate source with *C. acetobutylicum*. The carbohydrate source is selected from the group consisting of corn fiber, xylan, and mixtures of corn fiber and xylan, in a direct fermentation process without pretreatment or prior hydrolysis.

DETAILED DESCRIPTION OF THE INVENTION

The fermentation process of this invention involves the fermentation of a carbohydrate source by a strain of *C. acetobutylicum*. In general, any strain of *C. acetobutylicum* which is capable of fermenting a substantial proportion of unhydrolyzed xylan can be employed. A preferred strain for the use of this invention is the asporogenic strain of *C. acetobutylicum*, ATCC 39,236, which is described in detail in the European patent application, Publication No. 011683, published June 27, 1984. That disclosure is incorporated herein by reference in its entirety.

The carbohydrate feedstock used in the practice of this invention contains either corn fiber, or xylan, or a mixture of the two. It is employed as an aqueous suspension containing from about 1% to about 15% of these components on a dry solids basis.

The hemicellulose, xylan, is a naturally-occurring polymer of D-xylose which may contain varying amounts of other saccharide units. It is a component of many plants and is frequently obtained from larch wood.

Corn fiber, as noted above, is a by-product of the corn wet-milling industry. It is used primarily as an animal feed because of its protein content. When corn fiber is utilized in the process of this present invention, the unfermented solids remaining after the fermentation contain an even higher percentage of protein than does the corn fiber. This enhances the value of the residue from the fermentation as a source of animal feed.

When corn fiber or xylan is used as the only carbohydrate feedstocks for the fermentation by *C. acetobutylicum*, the fermentation product contains substantial amounts of acetic and butyric acids. However, these acids are readily converted to acetone and butanol if starch hydrolyzate is added to the fermentation mixture. The starch hydrolyzate can be added at the start of the fermentation or when the fermentation nears completion. When corn fiber is used as the substrate, it is preferable to add the starch hydrolyzate after the fiber has been fermented, since early addition of starch hydrolyzate suppresses fermentation of the arabinose portion of the hemicellulose in the corn fiber.

The noncarbohydrate nutrients needed for the fermentation can be supplied by addition of a small amount (from about 0.5% to about 2% by weight, dry basis) of corn steep liquor to the fermentation medium. Corn steep liquor, which is produced when corn is steeped in a dilute solution of sulfur dioxide, is available from the corn wet-milling industry. Optionally, the growth of the microorganism can be enhanced by the periodic addition of corn gluten, another by-product obtained from the wet milling of corn. Thus, the process of the present invention can be carried out using only low-cost by-products of the corn wet-milling industry.

The fermentation process of the present invention is initiated by adding an inoculum of vigorously growing cells of a strain of *C. acetobutylicum* to a sterile medium which comprises an aqueous slurry of the corn fiber and corn steep liquor.

Inoculum formation and the fermentation are carried out at a temperature of from about 24° C. to about 40° C. and at a pH of from about 4.5 to about 5.5. The reactions are run under anaerobic conditions using medium which has been sterilized by heat or other means well known in the fermentation art.

The following examples further describe the embodiments of this invention. All parts are by weight and all percentages are by weight unless expressly stated to be otherwise.

Concentrations of solvents, volatile acids, and carbohydrates were determined using high-performance liquid chromatography (HPLC). Components were analyzed chromatographically by elution with 0.006 N $H_2SO_4$ from a cation-exchange resin in the hydrogen form. The eluted components were detected by means of a differential refractometer, plotted on a recorder and quantitated using an electronic integrator. The area under the curve which represents the concentration of each component is determined as a percentage of the total area. The general procedure is that given in "Analysis of Carbohydrate Mixtures by Liquid Chromatography", *Am. Soc. Brew. Chem. Proc.*, 1973, pp. 43–46. The separations were made on a 1-foot HPX-87 column in the hydrogen form, available from Bio-Rad Laboratories, Richmond, Calif.

Starch in corn fiber was determined by hydrolysis of the starch with alpha-amylase followed by analysis of the hydrolyzate using a YSI analyzer, Model 27, equipped with a dual injection module, No. 2720. The analyzer is available from YSI Instruments, Yellow Springs, Ohio. The analytical procedure furnished by the manufacturer was followed.

EXAMPLE 1

An inoculum was prepared by adding cells of the asporogenic strain of *C. acetobutylicum*, ATCC 39,236, to an aqueous solution containing 6% dry basis of a 10 dextrose equivalent (D.E.) starch hydrolyzate and 1% dry basis of corn steep liquor. The strain of *C. acetobutylicum* was deposited with the American Type Culture Collection, Rockville, Md., on Nov. 9, 1982, and will be freely available to the public when any U.S. patent disclosing this strain is issued. A contract has been entered into with the American Type Culture Collection to maintain the culture for a period of 30 years from the deposit date. The 10 D.E. starch hydrolyzate is available from the Grain Processing Company, Muscatine, Iowa, as Maltrin M-100. The corn steep liquor is available from the Corn Products Unit of CPC International Inc., Englewood Cliffs, N.J., as Code E801. The culture was incubated for 24 hours at 35° C. to produce cells of *C. acetobutylicum* in their exponential growth phase. In this experiment, this inoculum was added on a 5% volume/volume basis to an aqueous suspension containing 10% dry basis corn fiber and 0.75% dry basis corn steep liquor. Fermentation was conducted at 35°–37° C. until gas evolution ceased (48–72 hours). The fermentation liquor was separated from the solid residue and analyzed by HPLC. The results are given in Table I, which also indicates the amounts of fermentable lactate present in the corn steep liquor. They show that about 40% of the fiber is fermented, much more than the 30% starch present in the fiber. The solid residue has a texture similar to that of the original corn fiber.

TABLE I

| CORN FIBER FERMENTATION BY *C. ACETOBUTYLICUM* | |
|---|---|
| | Grams |
| Feed | |
| Fiber | 4.59 |
| Lactate in Corn Steep Liquor | 0.09 |
| Total Feed | 4.68 |
| Total Starch in Feed | 1.38 |
| Solid Residue After Fermentation | 2.84 |
| Fiber Fermented | 1.84 (39.3%) |
| Fermentation Products | |
| Acetic Acid | 0.215 |
| Butyric Acid | 0.374 |
| Acetone | 0.116 |
| Butanol | 0.160 |
| Ethanol | 0.017 |

EXAMPLE 2

The procedure of Example 1 was followed on a scale 10 times that given in Example 1. The fermentation ceased after 48 hours. Analysis indicated that again about 40% of the corn fiber had been fermented. The solid residue recovered from the fermentation contained 16.2% protein in contrast to the starting corn fiber which contained 11.6% protein. This demonstrates that the residue obtained by the process has an enhanced protein value as a component of animal feed.

EXAMPLE 3

The fermentation of corn fiber was carried out according to the general procedure of Example 1. Samples of the fiber and the residue after completion of the fermentation were analyzed to determine how much of each of the carbohydrate fractions had been fermented. In order to determine the amount of starch present, the solid was digested with an alpha-amylase enzyme and the amount of dextrose released was measured using the YSI analyzer. The hemicellulose saccharides were determined on the solid remaining after the alpha-amylase hydrolysis. This solid was further hydrolyzed with 0.2 N $H_2SO_4$ at 121° C. followed by analysis of this hydrolyzate for xylose, galactose, and arabinose by HPLC. The saccharides of the fermented fiber residue were analyzed by similar methods. The hemicellulose analysis reports the sum of xylose and galactose as one value since these two sugars are eluted together in the HPLC procedure used. The results of this experiment, reported in Table II, show that over 99% of the starch present in the fiber is fermented. They also show that about 17% of the xylose plus galactose portions and 19% of the arabinose portion of the hemicellulose polymers are fermented.

TABLE II

| CORN FIBER COMPONENTS FERMENTED | | | |
|---|---|---|---|
| | Carbohydrate Components | | |
| | | Hemicellulose | |
| Sample | Starch (As g/l Dextrose) | (As g/l Xylose + Galactose) | (As g/l Arabinose) |
| Corn Fiber Slurry | 31.9 | 18.2 | 9.2 |
| Residue After 48-hr Fermentation | 0.1 | 15.1 | 7.4 |
| Carbohydrate Consumed (%) | 99.7 | 17.0 | 19.6 |

EXAMPLE 4

The procedure of Example 2 was followed except that the material being fermented also contained 2.8% on a dry solids basis of a 10 D.E. starch hydrolyzate and the fermentation was carried out for 96 hours. Analysis of the product showed that essentially all of the starch and starch hydrolyzate present had been fermented. In addition, about 17% of the xylose+galactose-containing fraction of the hemicellulose, as well as about 10% of the arabinose-containing fraction of the hemicellulose had been fermented. In an average of two runs, the fermentation liquors contained the following products on a grams per liter basis: acetic+butyric acid—4.4; acetone—6.3; butanol—15.1; ethanol—0.8. This example demonstrates that when starch hydrolyzate is added to the suspension of corn fiber, the fermentation proceeds to the solvent stage with the weight of solvents produced being about 31.5% of the weight of substrate consumed.

EXAMPLE 5

An anaerobic fermentation of larch wood xylan (Sigma Chemical Company, St. Louis, Mo.) by *C. acetobutylicum*, Strain ATCC 39,236, was carried out. A liter of the fermentation medium contained, on a dry solids basis, the following components: xylan—10 g; corn steep liquor—5 g; corn gluten—5 g; calcium carbonate—1 g; sodium thioglycollate—0.1 g. To 100 ml of the sterile medium in an anaerobic chamber was added a 5-ml inoculum of a rapidly growing culture of *C. acetobutylicum* prepared as in Example 1. After this culture had been incubated at 35° C. for 24 hours, a 10-ml inoculum was removed and added to a fresh 100 ml of sterile medium under anaerobic conditions. At periodic intervals, an aliquot portion of the fermentation liquor was removed and analyzed. All components except xylan were analyzed by HPLC. Xylan was analyzed as total carbohydrate using the phenol-sulfuric acid method with xylose as a standard. The results of these analyses are reported in Table III. The lactic acid is present as a constituent of the corn steep liquor. These results indicate that a substantial portion of the xylan has been fermented by *C. acetobutylicum*.

The general procedure of this example was repeated using fermentation media containing xylan at concentrations of 10, 25, and 50 g/l. In general, these fermentations consumed about 40% of the xylan. However, fermentations started slowly when the substrate contained higher concentrations of xylan and required a longer time for completion.

TABLE III

FERMENTATION OF XYLAN BY *C. ACETOBUTYLICUM*

| | Hours | Xylan (mg/ml) | Lactic Acid (mg/ml) | Acetic Acid (mg/ml) | Butyric Acid (mg/ml) | Xylose (mg/ml) |
|---|---|---|---|---|---|---|
| 1 | 0 | 9.44 | 1.30 | 0.25 | 0 | 0.35 |
| 2 | 8 | 8.83 | 1.30 | 0.30 | 0 | 0.82 |
| 3 | 24 | 7.54 | 0.55 | 0.65 | 1.15 | 0.30 |
| 4 | 32 | 7.00 | 0.50 | 0.70 | 1.20 | 0.30 |
| 5 | 48 | 6.06 | 0.20 | 0.80 | 1.65 | 0.23 |
| 6 | 72 | 3.80 | 0.00 | 0.90 | 2.45 | 0.050 |

What is claimed is:

1. A process for producing products selected from the group consisting of acetone, butanol and fatty acid, comprising fermenting an aqueous medium with a biologically pure culture of *clostridium acetobutylicum*, wherein the carbohydrate source is xylan, in a direct fermentation process without prior hydrolysis of said xylan.

2. The process of claim 1 wherein the strain of *clostridum acetobutylicum* is Strain ATCC 39,236.

3. The process of claim 2 wherein the carbohydrate source is xylan at a concentration in the medium of from about 1% to about 15% by weight on a dry solids basis.

4. The process of claim 2 wherein the aqueous medium comprises corn steep liquor.

5. The process of claim 4 wherein the aqueous medium further comprises corn gluten.

6. The process of claim 2 wherein the aqueous medium consists essentially of water, corn fiber, and corn steep liquor.

7. The process of claim 1 wherein the fermentation is carried out at a temperature of from about 24° C. to about 40° C.

8. The proces of claim 1 wherein the fermentation is carried out at a pH between about 4.5 and about 5.5.

* * * * *